(12) United States Patent
Paske (10) Patent No.: US 6,231,525 B1
(45) Date of Patent: May 15, 2001

(54) SYSTEM AND METHOD FOR PROVIDING QUANTIFIED HAND ANALYSIS

(76) Inventor: William C. Paske, 3331 Confederate Ct., Missouri City, TX (US) 77459-4913

( * ) Notice: Subject to any disclaimer, the term of this patent is extended or adjusted under 35 U.S.C. 154(b) by 0 days.

(21) Appl. No.: 09/425,885

(22) Filed: Oct. 25, 1999

(51) Int. Cl.[7] ............................. A61B 5/103; A61B 5/117
(52) U.S. Cl. ............................................................ 600/587
(58) Field of Search ................................... 600/587, 300, 600/595

(56) References Cited

U.S. PATENT DOCUMENTS

| | | | |
|---|---|---|---|
| 4,774,966 | 10/1988 | Lemmen | 128/774 |
| 5,002,065 | 3/1991 | LaCourse et al. | 128/739 |
| 5,012,817 | * 5/1991 | Zielinski et al. | 600/587 |
| 5,125,270 | * 6/1992 | Kovacevic | 600/587 |
| 5,157,970 | 10/1992 | Lewis, Jr. | 73/379 |
| 5,163,443 | 11/1992 | Fry-Welch et al. | 128/782 |
| 5,174,154 | * 12/1992 | Edwards | 600/587 |
| 5,230,345 | 7/1993 | Curran et al. | 128/739 |
| 5,301,683 | 4/1994 | Durkan | 128/744 |
| 5,325,869 | 7/1994 | Stokes | 128/779 |
| 5,447,167 | 9/1995 | Fleischaker | 128/782 |
| 5,471,996 | 12/1995 | Boatright et al. | 128/782 |
| 5,513,651 | 5/1996 | Cusimano et al. | 128/782 |
| 5,583,201 | 12/1996 | Cameron, Sr. et al. | 530/359 |
| 5,676,157 | 10/1997 | Kramer | 128/782 |
| 5,778,885 | 7/1998 | Doyama et al. | 128/782 |

OTHER PUBLICATIONS

W.C. Paske, Ph.D., et al.; *A Tool For Measuring Simultaneous Digital Forces: Medical Implications*; Feb. 11, 1999.

\* cited by examiner

*Primary Examiner*—Cary O'Connor
*Assistant Examiner*—Brian Szmal (57) ABSTRACT

A non-invasive system and method of determining the presence or absence of neural, muscular, soft tissue, bone or joint damage to a person's hand and/or wrist. The system includes a plurality of force members, one of which is engageable by the person's thumb and two of which are engageable by other digits of the hand, at least one of the other digits being innervated by the ulnar nerve. Force detectors are operatively connected to at least two of the force members for measuring the quantity of force applied through respective force members as the thumb and other digits are brought toward each other in a natural gripping motion. The measured forces are displayed for analysis of the hand and/or wrist.

24 Claims, 4 Drawing Sheets

Fig. 1  Fig. 1a $\angle 23 = \pi - \beta$
$\angle 24 = \pi - \gamma$

SYSTEM AND METHOD FOR PROVIDING QUANTIFIED HAND ANALYSIS

TECHNICAL FIELD

The present invention relates to a device for measuring both the absolute and relative muscular strength of the hand digits innervated by the median and ulnar nerves. In addition, the present invention provides a method by which the ratiometric strengths of the digits may be used to distinguish between repetitive motion injuries such as Carpal Tunnel Syndrome (CTS) and other neural or trauma induced injuries.

BACKGROUND OF THE INVENTION

Repetitive motion disorders such as carpal tunnel syndrome are the most common occupational illnesses being reported among a wide range of professions which involve significant hand/wrist motions such as typists (particularly forceful typists), meat cutters, etc. Carpal tunnel syndrome (CTS) symptoms include decreased strength; paresthesias (burning or tingling) in the thumb and adjacent fingers; pain in the wrist, palm, forearm; decreased median nerve conduction velocities; and sensory loss in areas of the hand innervated by the median nerve.

Symptoms resembling CTS may be due to chronic diseases such as rheumatoid arthritis or diabetes mellitus; congenital defects; acute trauma; age; birth control pill usage; and pregnancy. Historically, to aid in the diagnosis of the symptoms, Tinel's Sign, Phalen's Test, and Electromyography nerve conduction tests are usually conducted. Additional tests have been developed to aid in symptom diagnosis which are based on specific measurable parameters such as: the expected weakness of the diseased hand; the decreased sensitivity of the fingers to applied vibrational stimulus; restricted range of motion; sensitivity to applied pressure and chemical analysis of body proteins.

By lightly percussing the course of the median nerve for several seconds, a tingling sensation may be felt in the distribution of the median nerve, indicating a positive Tinel's Sign that suggests that CTS may be present. Phalen's Test generally requires the patient to press the backs of both hands together forming right angles, or holding the patient's wrist in acute flexion for 60 seconds. Numbness or tingling developing over the distribution of the median nerve is an indication that CTS is possible. Positive results in these tests are usually followed by electromyography (EMG) nerve conduction studies. An EMG is sensitive enough to detect the syndrome in 85% of those tested. However, a positive test result cannot be achieved in cases where the nerve has not been damaged to the extent that conduction has been impaired.

Presently, objective clinical information regarding the structure and functionality of the nervous system may be collected by recording electrical signals generated or propagated through the muscular or neural paths of interest. These electrodiagnostic tests require electrodes to be affixed to the patient under study so that electrical signals passing through the area of study may be collected and recorded. In general, these systems require the use of electrodes for both collection and stimulation, which may cause surface burns and/or pain to the patient during the evaluation. Two safety issues are present when using these tests: patient/practitioner contamination due to blood born infection, and possible electrical shock. Both of these hazards may be minimized through disposable electrodes and through proper electrical shielding to make the systems "touch- proof" (shock-proof).

To significantly augment the present electrodiagnostic methods, a methodology relying on totally different physics is necessary. The prior art, not relying on the art of electrodiagnostics, discloses several devices which measure a variety of parameters which are intended to provide evidence of injury, specifically CTS. These prior devices fall into distinct categories which rely or different physical concepts or address specific symptoms. These groups are:

Muscle Strength: Device measures the strength of the finger(s), thumb, or the whole hand grip.

Vibration Threshold: Device measures the threshold of the finger's sensitivity to applied vibrations.

External Pressure: Device applies an external pressure to the appropriate nerve pathway and then asks for subjective report of numbness or weakness.

Body Mobility: Device assesses range of motion in conjunction with EMG testing;

Chemical Analysis: Body fluids are extracted and analyzed via electrophoresis or immunoassay to measure relative amounts of proteins which may be used to infer injury.

U.S. Pat. No. 4,774,966 describes a muscle strength measurement. This device is intended to provide an objective method to measure any weakness present in the hand. If present, this weakness might be related to carpal tunnel syndrome and as such, provide an early identification of the problem. This measurement is accomplished by measuring the strength of the intrinsic hand muscles innervated by the median nerve after it passes through the carpal tunnel. The motion of the hand is limited by the fixture provided such that only the muscles supplied by the median nerve are measured. The test provides a screening by comparing the strength measured to a predefined normal strength. If the test individual should indicate weakness, further evaluation would be indicated. Weakness could be due to peripheral neuropathy, cerebral damage, cervical cord damage and neuromuscular disease.

U.S. Pat. No. 5,163,443 describes a muscle strength measurement. This invention provides for the measurement of applied forces exerted by the hand, wrist and forearm with the intention of detecting the presence of cumulative trauma disorders, such as CTS. The forces measured are correlated with forces expected or required in specific work tasks, by comparing maximal strength as well as mobility of the limb in question. In addition, the system will provide a grip and finger strength measurement. These measurements are made by a single transducer.

U.S. Pat. No. 5,471,996 describes a muscle strength measurement. This patent describes an apparatus which allows a measurement of the muscle strength of the thumb to be studied. Assessment of the strength of the abductor pollicis brevis is important in the diagnosis of some types of neck and elbow injuries, and for CTS and other hand disorders. This apparatus restrains the hand and allows restricted movement to guarantee a reproducible force is applied by the thumb. Isometric and isokinetic testing is possible with this apparatus.

U.S. Pat. No. 5,002,065 describes a vibration threshold measurement. Nerve injury may be induced by exposure to excessive vibration, causing the sensory threshold to be increased for the afflicted fingers. It has also been suggested that an increase in the perception threshold for vibration stimuli is the earliest detectable objective sign in patients with CTS. This patent teaches that serious injury caused by exposure to vibration may be prevented by predicting the injury to the hands prior to irreversible damage by observing the patient's threshold to vibrational stimuli. This same method may be used to measure sensory disturbances such as CTS. This invention provides for the application of a normalized vibrational stimulus to a finger of the patient. The frequency and amplitude of the stimulus are discrete and variable. As the test ensues and the frequency/amplitude are increased, the patient is requested to indicate the onset of sensory perception of the stimuli. The patient is also asked to indicate the loss of detection of the stimuli while the frequency/amplitude sweep is decreasing. The patent addresses the conditions of hand position, temperature, and uniform pressure during testing.

U.S. Pat. No. 5,230,345 describes a vibration threshold measurement. This patent provides for a system and method for detecting CTS in a patient by utilizing a vibratory waveform having a discrete frequency and a variable amplitude. The waveform is applied directly to the finger via contact with a speaker cone. A single finger is measured during the test procedure. When the stimuli is detected by the patient, the patient "clicks" the mouse which sends a control signal to the computer. This procedure is completed three times and the results averaged. The results are compared to a predetermined threshold baseline. Measurements exceeding the baseline indicate a diseased condition in the patient.

U.S. Pat. No. 5,301,683 describes an external pressure measurement. Direct pressure is applied for thirty seconds to the median nerve as it passes through the carpal tunnel at base of the wrist. Patients having anatomic evidence of CTS will experience and report numbness, pain, weakness or paresthesias in the distribution of the median nerve distal to the carpel tunnel. This patent provides a system and method for application and control of this applied pressure, so that repeatable tests may be accomplished.

U.S. Pat. No. 5,513,651 describes a body mobility measurement combined with a surface electromyography test. This patent uses a range of motion arm (ROMA) having six degrees of freedom to determine the range of motion in the upper and lower back while recording an exerting force on a strain gauge to simulate lifting conditions. This system will provide a non-invasive, non-loading test for analyzing myofacial injuries and repetitive stress injures. This invention will provide a means to look at the relationship between muscle groups to determine if the problem is cervical, CTS or cubital tunnel.

U.S. Pat. No. 5,583,201 describes a chemical analysis measurement. This invention provides for the diagnosis of peripheral nerve damage, including the damage which causes back and neck pain. A body fluid sample is extracted and subjected to a two-dimensional electrophoresis or an immunoassay. A diagnosis can be made by comparing the relative amounts of protein or proteins which increase or decrease in concentration to a standard control. This study determines whether the pain is caused by muscle or fibrous tissue injury.

The measurements described above relating to the strength of the muscles under study use predetermined standards of what is considered normal. The measurements are also limited to the muscle groups innervated by the median nerve. Since the hand also involves the ulnar nerve (third and fourth finger), these measurements are not conclusive. Individual strength variations due to relative degree of muscle tone could also mitigate these studies. The measurements relating to vibration sensitivity rely on the patient's compliance to provide an accurate threshold determination. The external pressure measurement described also relies on patient response. The mobility measurements described uses EMG measurements in conjunction with the range of motion tests to remove the patient's subjective involvement. The chemical assay methodology described does not require the patient's compliance, but is invasive.

SUMMARY OF THE PRESENT INVENTION

The present invention provides a system for measuring force applied by digits of the hand as a function of time and as a function of the hand-wrist position (e.g., flexed or neutral). This invention provides a method which determines the muscle fatigue rates and the relative coordination exhibited by the digits under study. The applied forces are measured using suitable force detectors such as strain gauges which may be accurately calibrated to provide long term trend studies of the subject hand(s). These detectors are placed onto a fixture which is held by the subject, allowing the subject hand to open and close in a manner "normal" for that hand. The subject is asked to perform a series of finger tip squeeze motions which could range from a single squeeze held as long as the subject is capable to a series of squeeze, release, squeeze, release patterns which may last from a few seconds to several minutes. The forces exerted by the subject are recorded and stored for analysis.

For an effective analysis of the hand, the thumb and at least two other fingers must be involved in a test. Measurements must be made from at least two digits, one of which is innervated by the median nerve (thumb, first, second and third fingers) and one of which is innervated by the ulnar nerve (third and fourth fingers), the third finger being innervated by both the median and ulnar nerves.

A preferred embodiment of the invention measures the triad forces applied by the thumb opposed by the first and fourth fingers, forming a triangular force system. The thumb must balance the forces exerted by the two fingers. How this balance is accomplished by the subject provides information concerning the health of the muscles and nerves involved in the measurement. By forming a triangle as described, problems residing in the median nerve but not in the ulnar nerve (or vice versa), or in both nerve paths, are clearly delineated. The presence or absence of pain will also effect the way in which these forces are balanced. Cross plots of all possible pairs of the measured forces provide diagnostics which may also infer hand coordination. In this embodiment, the data sample times are fast enough to resolve time increments of 13 ms. Poor coordination between any two of the measured digits is demonstrated by very erratic cross plots produced by jerky hand motions. The muscle fatigue may be determined from these data by computing the rate of decay or force attenuation as a function of the time that the forces are applied. All of these parameters, applied force, coordination, fatigue, etc, may be determined as a function of minutes, hours, days, weeks, or even years. In this manner, documentation is provided concerning the relative and absolute health of the subject's hand(s).

These measurements may be made using different hand-wrist configuration so that differences observed in the subject's hand response may be correlated to position as desired. This would be useful in the cases where nerve damage detectable by electrodiagnostic methods has not yet occurred but pain is reported by the subject. Differences in the subject's test results with the hand-wrist in the neutral position verses a flexed position would help quantify the diagnosis.

In other embodiments, springs, air bags, or other like instruments may be placed on or under the force detectors of the hand fixture to allow a measurement of both the applied force and the displacement caused by the force. The displacement would be useful in studying or in determining types of motion responsible for any detected injury.

Thus, the objects of the present invention are to provide rapid, non-invasive, reproducible, quantifiable measurements for the following:

Relative and absolute digit strength for the hand(s) under study, which may be compared to tests completed months or years earlier in a statistically significant manner.

Muscle fatigue rates so that long term studies will be able to discern improvement or degradation of the hand(s).

Measure relative hand coordination which will provide quantified documentation for improvement or degradation of the hand(s).

Provide measurements which will clearly support or defeat claims of muscle or nerve damage related to repetitive motion injury, carpal tunnel injury, trauma, or other neural disorder.

Other objects and advantages of the invention will be apparent from reading the description which follows in conjunction with the accompanying drawings.

BRIEF DESCRIPTION OF THE DRAWINGS

FIG. 2 is a force diagram showing the determination of the critical angles of forces applied with the fixture of FIG. 1 and determined as in FIG. 1a;

FIG. 4b is a comparative plot of force versus elapsed time measurements-for the fourth finger of a person utilizing the same system as with FIG. 4a.

DETAILED DESCRIPTION OF A PREFERRED EMBODIMENT OF THE INVENTION

Figure 1:
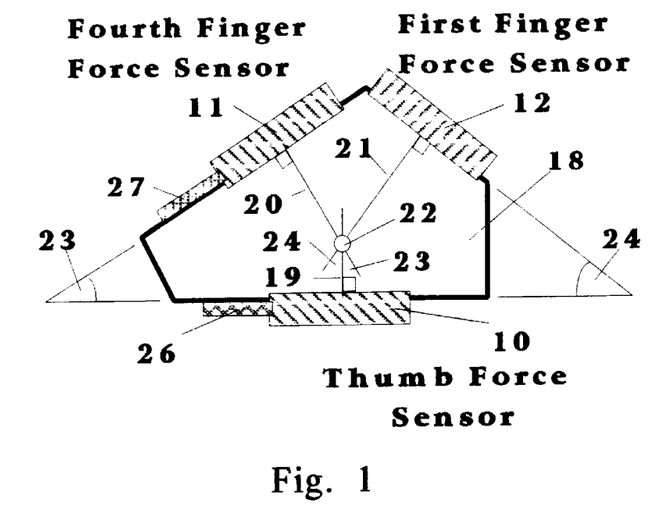
FIG. 1 is a schematic representation of an adjustable fixture which supports the force detectors used in the non-invasive system and method of the present invention for determining the presence or absence of neural damage to a person's hand and/or wrist, according to a preferred embodiment thereof.

A schematic representation of a force sensor fixture is shown in FIG. 1. This fixture 18, may be made from a solid block of material or made to be adjustable to accommodate more than one individual subject. The important feature of this fixture is to adjust the placement of the force sensors or detectors, 10, 11 and 12, such that their alignment is perpendicular to the "normal" gripping motion of the test subject's hand or fingers. These detectors need to be aligned by the adjustments represented at 26 and 27 such that the force projections, 19, 20, and 21, meet at a point 22. This geometry minimizes side-loading of the sensors out of the plane of the fixture and ensures that the stability of the fixture 18 may be easily controlled by the test subject. This configuration also allows any side loading present in the plane of the fixture due to poor hand coordination to be trigonometrically resolved.

Figure 1A:
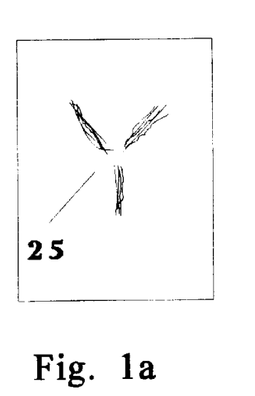
FIG. 1a represents marking on paper by a test subject to determine critical angles of motion between digits thereof.
Figure 2:
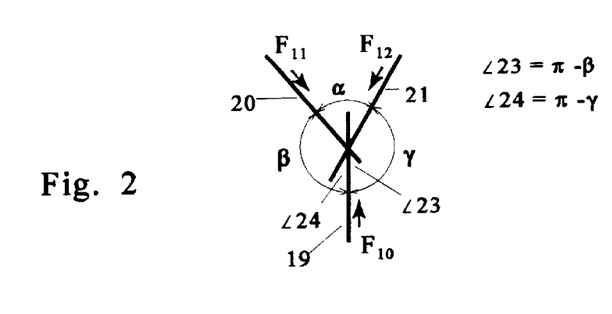

A solid block has the advantage of being very rigid, reducing elastic compression of the fixture during compression of the force sensors. An adjustable fixture has the advantage of being useful for more than one individual. The critical angles, 23 and 24, may be determined by noting the "normal" motion of the test subject's digits via a method similar to the following. Attach pencils, pens, chalk, etc to the test digits of interest; e.g., the thumb, first and fourth fingers. Ask the test subject to repeatedly scratch on a piece of paper, forming a pattern similar to that shown at 25 in FIG. 1a. By averaging the marks shown in 25, the angles 23 and 24 may be determined by trigonometric means as shown in FIG. 2. After adjusting the angles 23 and 24, the force detectors need to be adjusted by 26 and 27 to ensure that the perpendicular projections, 19, 20 and 21, meet at point 22. Similarly, the angles 23 and 24 may be determined electronically by holding a device which can infer the angles subtended during the gripping motion.

The fixture is lightly held by the test subject by placing the fingertips of the test digits on the force detectors. This fixture then defines a plane through which the forces must act in order to maintain a grip on the fixture. The fixture should NOT be held by the finger or thumb joints, as this defeats the balance required for the measurements. The fixture does not limit the hand-wrist orientation, and this orientation may be varied to aid in diagnosis of any suspected illness or injury. This embodiment of the fixture requires that muscle groups innervated by the ulnar and median nerves will work in opposition in order to balance the fixture. Problems present in one or the other, or both nerve systems will be evident in how the digits balance the fixture during tests. Strength of the test subject's hand is not critical since comparative measurements will be made for all three digits. However, due to the fixture geometry, the force exerted by the thumb on the thumb force sensor will always equal the forces exerted by both finger force sensors. This force balance is shown in FIG. 2 and by the equations Eq. (1) and Eq. (2) below. These equalities will provides a constant quality check on the sensor calibrations. The angle 23 is given by $\pi-\beta$ and the angle 24 is given by $\pi-\gamma$, expressed in radians.

$$0 = F_{12} \cdot \sin(\pi-\gamma) + F_{11} \cdot \sin(\pi-\beta) \qquad \text{Eq. (1)}$$

$$F_{10} = F_{12} \cdot \cos(\pi-\gamma) + F_{11} \cdot \cos(\pi-\beta) \qquad \text{Eq. (2)}$$

Figure 3:
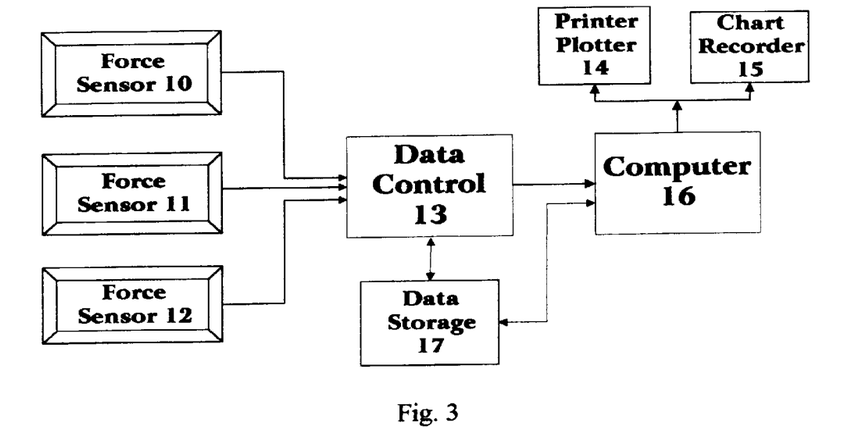
FIG. 3 is a block schematic representing the components used during measurement and display of a preferred embodiment of the invention.

Referring now to FIG. 3, to conduct a test, the subject lightly holds the fixture maintaining the hand-wrist in a prescribed orientation. Fixtures such as bowling or golf braces may be used to help maintain the hand wrist orientation of choice. Upon timing prompts (visual and/or audible) provided by the data control module 13, the test subject squeezes the force sensors, 10, 11, and 12, using only the finger tips. As the test ensues, the data controller 13, collects the data and sends it to storage 17, for later analysis, or to the computer 16 for immediate processing. After processing the data, the results of the test are displayed on the computer 16, printed and/or plotted, 14, 15, and saved to disk 17. The raw data is also available for display on 15 or on the computer 16. Many variations and combinations of regular or irregular squeezes may be studied. Short one or two second squeezes may be repeated for several minutes, or longer squeezes held for five or ten seconds may be repeated for several minutes or a single long pulse of several minutes may be studied. In this manner, hand strength, muscle fatigue, and coordination may be quickly ascertained in a quantifiable, documented manner.

Figure 4A:
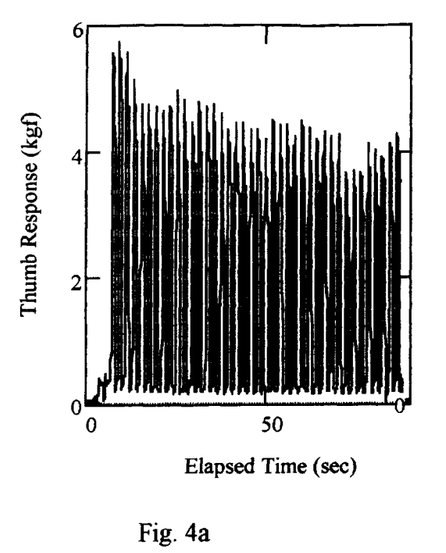
FIG. 4a is a plot of force versus elapsed time measurements for the thumb of a person utilizing the system of the present invention, according to a preferred embodiment thereof.
Figure 4B:
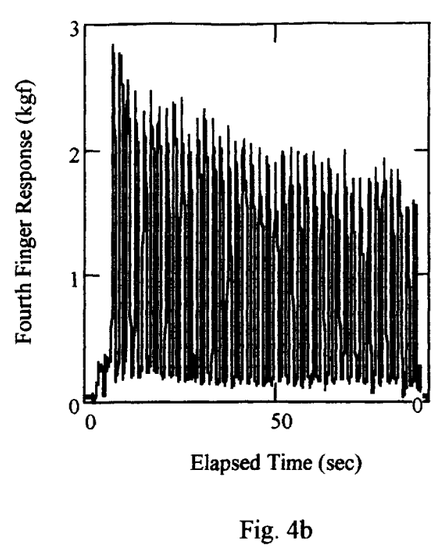
Figure 4C:
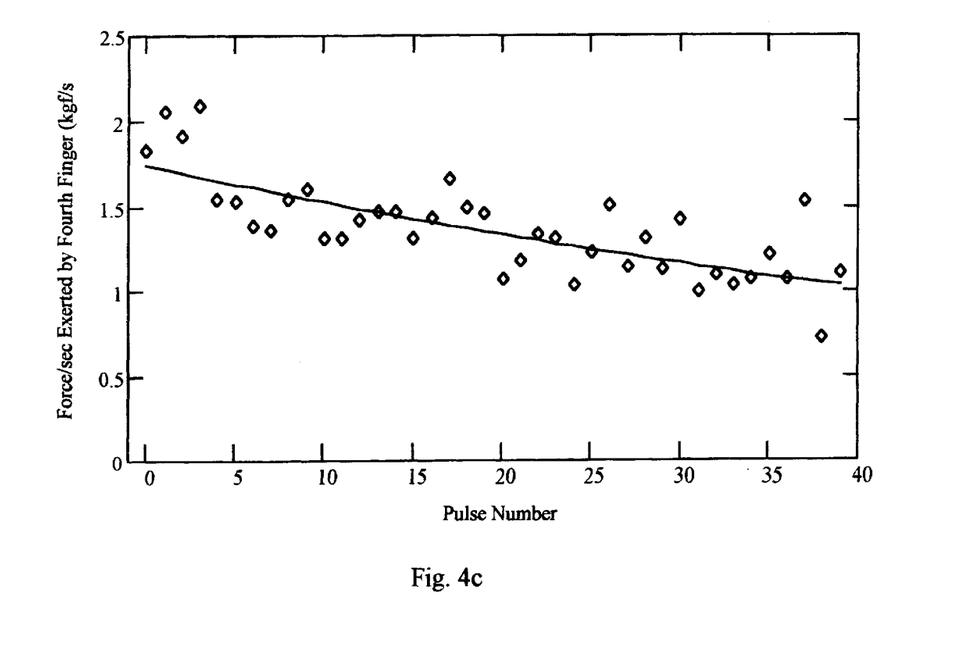
FIG. 4c is a plot of force versus pulse representing muscle fatigue of the fourth finger over a period of time.

Strength and Fatigue:

Referring now to FIGS. 4a, 4b and 4c, the applied force data has been collected and displayed for the thumb (FIG. 4a) and the fourth finger (FIG. 4b) as a function of elapsed time. Both plots show a decrease in the applied force (kgf) as a function of elapsed time (sec). If the short term rate of fatigue is defined as $\lambda$, a short term fatigue rate may be computed from the data using Eq. (3):

$$\lambda = \frac{1}{t} \cdot \ln\left(\frac{F}{F_o}\right) \qquad \text{Eq. (3)}$$

where:

t=elapsed time in seconds

F=Force applied by the digit of interest at a time t $F_o$=Zero time force intercept, or approximately the initial applied force.

The best manner by which to determine this fatigue rate would be using standard curve fitting techniques, as shown in FIG. 4c, which is a re-plot of the data in FIG. 4b with the pulses integrated and plotted as a function of the pulse number, and in this data set, each pulse represents a time step of 2.31 seconds. In this case the term $F_o$ is the intercept and $\lambda$ would be the slope determined by a least squares exponential fit to the data. Long term fatigue rates may also be determined in a similar manner. Data collected over many minutes, e.g., 15 or 20 minutes, may be used to numerically or graphically determine a long term fatigue rate in like manner. To date, studies have shown that for compliant subjects, the short term fatigue rates collected over 40 seconds are quite similar if not identical to long term fatigue rates collected over 20 minutes. This similarity thereby provides a subject compliance check throughout the tests.

The absolute and ratiometric strengths of the digits involved in the tests may be determined as time averages or as time dependent parameters which may be determined by computing the ratios, ($R_{1T}$, $R_{4T}$, $R_{14}$) of the applied forces as defined by Eq. (4):

$$R_{1T} = \frac{F_1}{F_T}; \qquad \text{Eq. (4)}$$

$$R_{4T} = \frac{F_4}{F_T};$$

$$R_{14} = \frac{F_1}{F_4}$$

where:

$F_1$=the force applied by the index (first) finger, $F_4$=the force applied by the fourth finger, $F_T$=the force applied by the thumb.

Comparisons made between the digits of interest as a function of time can also provide the absolute muscle strength tests as in prior art but without the need to compare to a predetermined strength data base. Regardless of the strength of the individual, the ratiometric ratios and the fatigue measurements provide documentation on a specific subject, independent of prior training or abilities. In addition, a non-compliant subject would have to repeat the ratiometric strength results with the appropriate fatigue rates to provide convincing proof of an injury or illness.

Figure 5A:
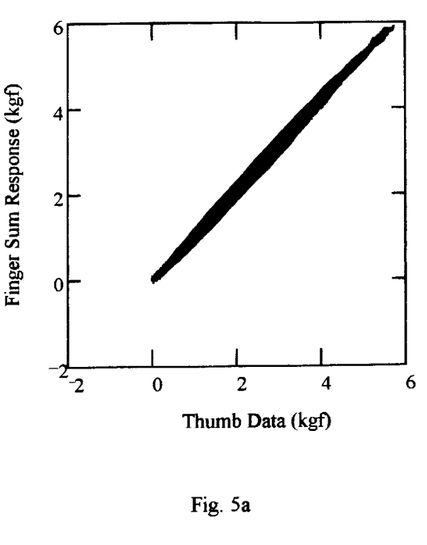
FIGS. 5a through 5d is a sequence of plots showing the ratiometric strengths and coordination abilities of the test subject, FIG. 5a representing a quality check by comparing the sum of the finger forces to the opposing thumb force, FIG. 5b representing the data collected for the first and fourth fingers, FIG. 5c representing the data collected for the first finger and the thumb and FIG. 5d representing the data collected for the fourth finger and the thumb.
Figure 5B:
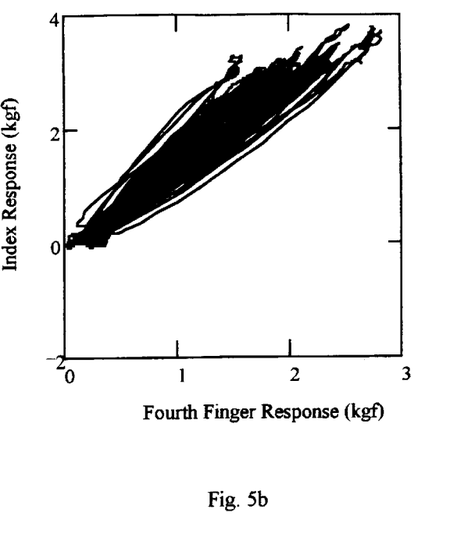
Figure 5C:
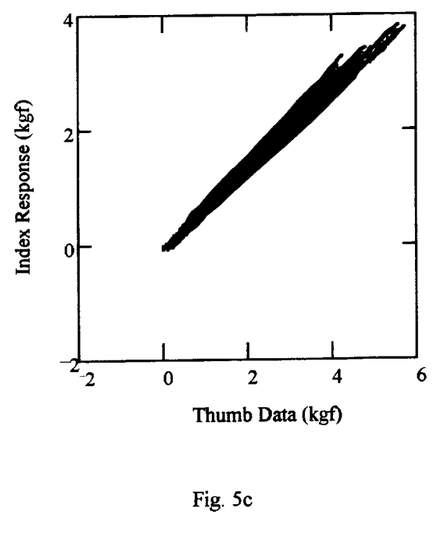
Figure 5D:
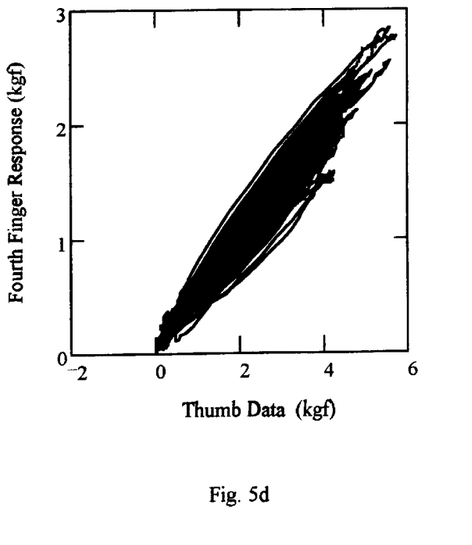

Coordination:

Referring now to FIGS. 5a through 5d, comparisons are being made between the applied forces exerted by the thumb, first and fourth fingers. The force applied by each digit is plotted with respect to a different digit. FIG. 5a shows a quality data check plot. In this plot, the sum of the forces applied by the index and fourth fingers is plotted against the force applied by the thumb. The Pearson's correlation coefficient for these data is r=0.9996 for the 7132 data points used in this test, indicating a good quality test was completed. FIG. 5b shows the crossplot of the forces applied by the index finger (median nerve) versus the fourth finger (ulna nerve). The correlation coefficient is r=0.9820 with n=7132. The crossplot between the thumb and the index finger is shown in FIG. 5c with r=0.9984 and the fourth finger versus thumb data is shown in FIG. 5d where r=0.9904. The data collected in FIGS. 5a through 5d were collected with the hand-wrist in the neutral position from a test subject with no known neural damage to the hand, but trauma injury was known to have occurred in the past due to a sports injury. Note the increased spread in the data collected for the fourth finger when plotted against the thumb and index finger. At the same time, the data between the index finger and thumb is quite narrow. This method of presenting the data allows the practitioner to discriminate between injury to specific digits. These tests could have been run using the second or third finger if injury was suspected to those digits. The only requirement is that the proper pair of fingers is chosen to ensure different nerve groups are used in the test. When coupled with hand-wrist positional tests, i.e., neutral versus flexed, a powerful diagnostic screen is provided.

Figure 6A:
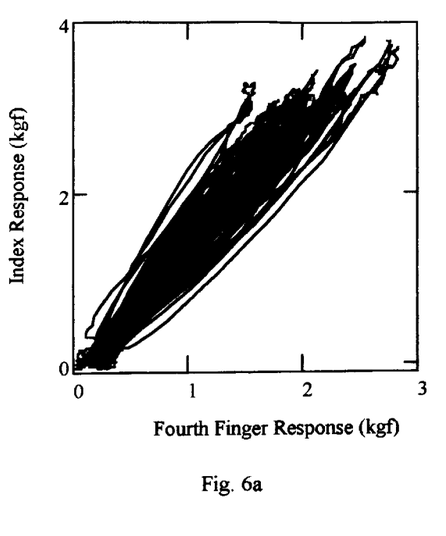
FIGS. 6a and 6b are comparison plots of the measured response between the first (index) finger and the fourth finger for two individuals, FIG. 6a representing applied force and the relatively smooth response of a normal hand, FIG. 6b representing the very erratic behavior in a hand previously diagnosed as suffering from CTS.
Figure 6B:
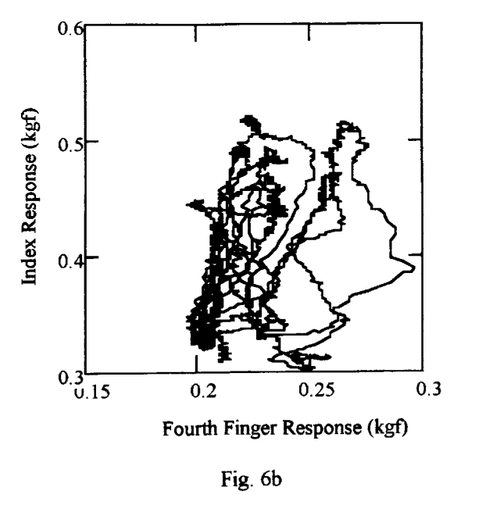

The effectiveness of this screen is shown in FIGS. 6a and 6b. In this case, the data is shown for the index versus fourth finger for the subject in FIG. 5b versus an individual with a known history of CTS. The correlation coefficient for FIG. 6b is r=0.4629, n=5200. Several important points are evident from these crossplots. The subject hand shown in FIG. 6b is weak, very erratic and poorly coordinated. Even without further testing, a problem is evident.

The method presented provides an indication as to the ratiometric strengths of the digits and as to the relative coordination abilities present between the digits of the hand. Compliance would not be an issue during these tests. Attempts by several individuals with no history of CTS to duplicate the results shown in FIG. 6b have failed to date. This is due to the natural coordination present in a properly functioning hand. Attempts to "jitter" the data by rapidly changing the applied forces fail because the finger movements are still coordinated on the measurement time scale. Only when the coordination is impaired by poor neural feedback will the data exhibit the erratic behavior shown in the figure.

The system and methods of the present invention are not limited to application to individuals afflicted with CTS. Any disease or injury of the hand may be evaluated by these methods. Since different nerve groups are studied, differential results indicate specific problems. For example, strength and fatigue rates of Multiple Sclerosis patients may be evaluated by these methods, providing documentation as a function of time. In fact, the time and/or frequency related outputs provided by the system of the present invention may be studied and used as diagnosis of specific hand, wrist, arm diseases using pattern recognition, neural networks, frequency analysis, signature analysis, plotting or graphic displays for visual analysis by trained doctors/medical technicians. The tests described herein may be repeated at hourly, daily, weekly, yearly or other intervals to determine long term effects.

The exemplary embodiment and method of the invention described with reference to the drawings utilizes the thumb, first and fourth fingers. Measurements are made from all three, the thumb and first finger for the median nerve and the fourth finger for the ulnar nerve. Other embodiments of the invention may involve the thumb and any of the other hand digits, or any other three contact points requiring muscle control by muscles innervated by different nerves. However, measurements must be made from at least two digits which involve different nerves, e.g. the median and the ulnar nerves.

In addition, the force sensors or detectors such as 10, 11 and 12 of FIG. 1, may be adapted with springs, air bags or the like to provide measurements of displacement caused by force exerted by the hand digits. In some cases the fixture might actually include or simulate devices normally used by the tested subject; e.g. a mouse, computer pointing device, computer keyboard, etc. This could lead to redesign or altered use of such devices.

While the forgoing disclosure and description of the invention is illustrative and explanatory thereof, various changes in the method steps as well as the details of the illustrated preferred embodiment may be made without departing from the spirit of the invention. Accordingly, it is intended that the scope of the invention be limited only by the claims which follow.

What is claimed is:

1. A system for objective, repeatable, non-invasive analysis of a person's hand and/or wrist to determine the presence or absence of neural, muscular, soft tissue, bone or joint damage thereto, said system comprising:

three or more force members one of which is engageable by the thumb of said person's hand and two of which are engageable by other digits at least one of which is innervated by the ulnar nerve and through which forces exerted in moving said thumb and other digits toward or away from each other in natural gripping and releasing motions may be transmitted, force detector means operatively connected to at least two of said force members one of which is engaged by an ulnar nerve innervated digit and one of which is engaged by a median nerve innervated digit, for measuring the quantity of force applied through said force members by a respective thumb or other digit of said person's hand and for producing outputs indicative of the forces generated by said digits; and display means for displaying said outputs.

2. The system of claim 1 in which said three or more force members are operatively aligned in a fixture so that an engageable surface of each of said force members is perpendicular to the force exerted thereto by its respectively engaging digit as said digits are moved toward or away from each other in said natural gripping and releasing motions of said person's hand.

3. The system of claim 2 in which said force members are operatively aligned in said fixture so that the projection of forces transmitted through each of said force members meet at a point between said force members.

4. The system of claim 3 in which said force members are adjustable within said fixture to allow proper alignment of said force members for persons of differing hand configuration and gripping and releasing motions.

5. The system of claim 1 in which said force members are of a rigid, relatively noncompressible material.

6. The system of claim 1 in which said force detector means and said display means are cooperatively connected to display said outputs in a time frequency related manner indicative of the forces generated by said digits during repetitive gripping and releasing motions of said person's hand.

7. The system of claim 1 in which said force detector means and said display means are cooperatively connected to display said outputs in a time related manner indicative of the forces generated by said digits during the duration of prolonged gripping or releasing of said person's hand.

8. The system of claim 1 in which said force members include one for each of said thumb, the first finger and the fourth finger of said person's hand, said force members being engageable by the pads of the fingertips of a respective thumb or finger.

9. The system of claim 8 in which said force members are operatively aligned in a fixture so that the surface of each force member engaged by the respective fingertip of said thumb or finger is perpendicular to the force exerted thereto by its respective said thumb or finger as said thumb and said first and fourth fingers are moved toward each other in said natural gripping and releasing motions of said person's hand.

10. The system of claim 9 in which said force members are operatively aligned in said fixture so that the projection of forces transmitted through each of said force members meet at a point between said force members.

11. The system of claim 8 in which said force members are operatively aligned in said fixture so that the projection of forces transmitted through each of said force members meet at a point between said force members.

12. The system of either claim 10 or claim 11 in which said force members are adjustable within said fixture to allow proper alignment of said force members for persons of differing hand configuration and gripping or releasing motions.

13. The system of claim 8 in which said force detector means is operatively connected to the force members for each of said thumb, first finger and fourth finger.

14. The system of claim 1 including displacement measuring means operatively connected to one or more of said force members for measuring the displacement of said one or more of said force members as said thumb and other digits are moved toward or away from each other.

15. A non-invasive method of determining the presence or absence of neural, muscular, soft tissue, bone or joint damage to a person's hand and/or wrist, the method comprising the steps of:

(a) having said person engage, with the pads of the tip of at least three digits of said hand, respective ones of three or more force transmitting members which are operatively aligned so that the surface of each of said force members is perpendicular to the force exerted thereto by its respectively engaging digit;

(b) having said person move said digits toward or away from each other as said person closes or opens said hand in natural gripping and releasing motions;

(c) measuring the force transmitted to at least two of said force transmitting members, one of which is engaged by a median nerve innervated digit and one of which is engaged by an ulnar nerve innervated digit, to provide quantifiable outputs therefor; and (d) displaying said quantifiable outputs representing the forces exerted by at least two digits innervated by differing nerves.

16. The method of claim 15 in which said person keeps said hand closed or opened for a prolonged period of time.

17. The method of claim 15 in which said person respectively moves said hand in gripping and releasing motions.

18. The method of claim 16 or claim 17 in which said measuring of said forces and displaying of said quantifiable outputs is conducted in a manner to produce outputs in a time and/or frequency and/or phase related display.

19. The method of claim 18 in which said quantifiable outputs are processed by computer means for storage or immediate use.

20. The method of claim 18 in which said time and/or frequency and/or phase related outputs are studied and used as diagnosis of specific hand, wrist and arm diseases or injuries using one or more of the following: pattern recognition, neural networks, frequency and/or phase analysis, signature analysis, plotting or graphic displays for visual analysis.

21. The method of claim 20 in which steps (a), (b), (c), and (d) are repeated at hourly, daily, weekly, yearly or other intervals to determine long term effects of said diseases or injuries.

22. The method of claim 18 in which a visual or audible signal is produced to indicate to said person when they should move said hand in said gripping and releasing motions.

23. The method of claim 15 in which said force transmitting members are provided on an existing tool or instrument to allow relative force/displacement measurements to be made while the tool or instrument is being used in the normal way by the person.

24. The method of claim 23 in which ergometric design of said tool or instrument is studied and optimized by selective placement of said force transmitting members on said tool or instrument to determine normalized forces on and displacement of said tool or instrument in actual use.

* * * * *